United States Patent
Mabon et al.

(10) Patent No.: US 12,398,043 B2
(45) Date of Patent: Aug. 26, 2025

(54) ZEOLITE SYNTHESES USING DIQUATERNARY STRUCTURE DIRECTING AGENTS

(71) Applicant: ExxonMobil Technology and Engineering Company, Spring, TX (US)

(72) Inventors: Ross Mabon, Whitehall, PA (US); Allen W. Burton, Stewartsville, NJ (US); Hilda B. Vroman, Piscataway, NJ (US); Simon C. Weston, Annandale, NJ (US)

(73) Assignee: EXXONMOBIL TECHNOLOGY AND ENGINEERING COMPANY, Spring, TX (US)

(*) Notice: Subject to any disclaimer, the term of this patent is extended or adjusted under 35 U.S.C. 154(b) by 0 days.

(21) Appl. No.: 18/733,491

(22) Filed: Jun. 4, 2024

(65) Prior Publication Data

US 2024/0317594 A1    Sep. 26, 2024

Related U.S. Application Data

(62) Division of application No. 17/635,420, filed as application No. PCT/US2020/043005 on Jul. 22, 2020, now Pat. No. 12,037,255.

(60) Provisional application No. 62/892,261, filed on Aug. 27, 2019.

(51) Int. Cl.
C01B 37/00 (2006.01)
C01B 39/48 (2006.01)
C07C 211/09 (2006.01)

(52) U.S. Cl.
CPC ............ C01B 39/48 (2013.01); C07C 211/09 (2013.01); C01P 2002/72 (2013.01)

(58) Field of Classification Search
None
See application file for complete search history.

(56) References Cited

U.S. PATENT DOCUMENTS 7,108,843 B2 * 9/2006 Zones .................... C01B 39/026
423/706

* cited by examiner

Primary Examiner — Sheng H Davis
(74) Attorney, Agent, or Firm — Shook, Hardy & Bacon L.L.P.

(57) ABSTRACT

A method can include heating an aqueous reaction mixture comprising a silicon source and a boron source and/or an aluminum source in the presence of a quaternary structure directing agent to a temperature of at least 75° C. to produce a zeolite. A composition can include a borosilicate zeolite, an aluminosilicate zeolite, or an aluminoborosilicate zeolite having a framework symmetry of C2/m and a unit cell with measurements of a of 3.5 Å to 4.5 Å, b of 20.1 Å to 21.1 Å, c of 15.5 to 16.5 Å, and β of 97° to 98°.

1 Claim, 3 Drawing Sheets

ZEOLITE SYNTHESES USING DIQUATERNARY STRUCTURE DIRECTING AGENTS

BACKGROUND

The present disclosure relates to a zeolite composition, methods for its preparation using quaternary directing agents, and its use in organic conversion and sorption processes.

Zeolitic materials are known to have utility as sorbents and to have catalytic properties for various types of hydrocarbon conversion reactions. Certain zeolitic materials are ordered, porous crystalline materials having a definite crystalline structure as determined by X-ray diffraction, within which there are a large number of cavities, which may be interconnected by a number of still smaller channels or pores. These cavities and pores are uniform in size within a specific zeolitic material. Since the dimensions of these pores are such as to allow for sorption molecules of certain dimensions while blocking those of larger dimensions, these materials have come to be known as "molecular sieves" and are utilized in a variety of ways to take advantage of these properties.

Such molecular sieves, both natural and synthetic, include a wide variety of crystalline silicates and substituted silicates, in which the silicon is partially or completely replaced by other tetravalent elements. These silicates can be described as a rigid three-dimensional framework of $SiO_4$ tetrahedra and optionally tetrahedra of a trivalent element oxide, e.g., $AlO_4$ and/or $BO_4$, in which the tetrahedra are cross-linked by the sharing of oxygen atoms whereby the local ratio of the total trivalent element and silicon atoms to oxygen atoms is 1:2. The electrovalence of the tetrahedra containing the trivalent element is balanced by the inclusion in the crystal of an extra framework cation, for example, an alkali metal or an alkaline earth metal cation. This can be expressed wherein the ratio of the trivalent element (e.g., aluminum) to the number of charges from various cations, such as $Ca^{2+}$, $Sr^{2+}$, $Na^+$, $K^+$ or $Li^+$, is equal to unity. One type of cation may be exchanged either entirely or partially with another type of cation utilizing ion exchange techniques in a conventional manner. By means of such cation exchange, it has been possible to vary the properties of a given silicate by suitable selection of the cation.

Molecular sieves that find application in catalysis include any of the naturally occurring or synthetic crystalline molecular sieves. Examples of these molecular sieves include large pore zeolites, intermediate pore size zeolites, and small pore zeolites. These zeolites and their isotypes are described in "Atlas of Zeolite Framework Types", eds Ch. Baer ocher, L. B. McCusker, D. H. Olson, Elsevier, Sixth Revised Edition, 2007, which is hereby incorporated by reference. A large pore zeolite generally has a pore size of 6-7.5 Å and includes LTL, VFI, MAZ, FAU, OFF, *BEA, and MOR (note that many of these frameworks, e.g., BEA and MOR do not have 7.0 Å pores) framework type zeolites (IUPAC Commission of Zeolite Nomenclature). Examples of large pore zeolites include mazzite, offretite, zeolite L, VPI-5, zeolite Y, zeolite X, omega, and beta. An intermediate pore size zeolite generally has a pore size from about 5 Å to less than 7 Å and includes, for example, MFI, MEL, EUO, MTT, MFS, AEL, AFO, HEU, FER, MWW, and TON framework type zeolites (IUPAC Commission of Zeolite Nomenclature). Examples of intermediate pore size zeolites include ZSM-5, ZSM-11, ZSM-22, MCM-22, silicalite-1, and silicalite-2. A small pore size zeolite has a pore size from about 3 Å to less than 5 Å and includes, for example, CHA, ERI, KFI, LEV, and LTA framework type zeolites (IUPAC Commission of Zeolite Nomenclature). Examples of small pore zeolites include ZK-4, SAPO-34, SAPO-35, ZK-14, SAPO-42, ZK-21, ZK-22, ZK-5, ZK-20, zeolite A, chabazite, zeolite T, and ALPO-17.

Many zeolites are synthesized in the presence of an organic structure directing agent, such as an organic nitrogen compound. For example, ZSM-5 may be synthesized in the presence of tetrapropylammonium cations. and zeolite MCM-22 may be synthesized in the presence of hexamethyleneimine.

SUMMARY

The present disclosure relates to a zeolite composition, methods for its preparation using quaternary structure directing agents (SDAs), and use of said zeolites in organic conversion processes.

A first example embodiment is a method comprising: heating an aqueous reaction mixture comprising (a) a silicon source and (b) a boron source and/or an aluminum source in the presence of a structure directing agent to a temperature of at least 75° C. to produce a zeolite, wherein the structure directing agent is represented by Formula 1:

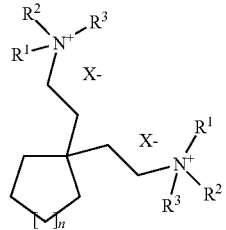

Formula 1 wherein n is 1 or 2; each of $R^1$ and $R^2$ is independently methyl or ethyl, or $R^1$ and $R^2$ are joined to form a pyrrolidinium or piperidinium ring; $R^3$ is methyl or ethyl; and $X^-$ is $OH^-$, $F^-$, $Cl^-$, $Br^-$, or $I^-$.

A second example embodiment is a composition comprising: a borosilicate zeolite, an aluminosilicate zeolite, or an aluminoborosilicate zeolite having a framework symmetry of C2/m and a unit cell with measurements of a of 3.5 Å to 4.5 Å, b of 20.1 Å to 21.1 Å, c of 15.5 to 16.5 Å, and β of 97° to 98°.

A third example embodiment is a composition comprising a borosilicate zeolite having a micropore volume of about 0.24 cm³/g to about 0.28 cm³/g and having an X-ray diffraction pattern including d-spacings and relative intensities of:

| d-spacing (Å) | Relative Intensity |
| --- | --- |
| 13.2-13-5 | SM |
| 11.9-12.2 | S |
| 11.5-11.8 | S |
| 10.3-10.6 | SM |
| 9.95-10.2 | S |
| 4.20-4.27 | SM |
| 3.92-3.96 | SM |
| 3.87-3.92 | VS |
| 3.04-3.08 | W |

A fourth example embodiment is a composition comprising a borosilicate zeolite, an aluminosilicate zeolite, or an aluminoborosilicate zeolite having a micropore volume of about 0.24 cm³/g to about 0.28 cm³/g and having an X-ray diffraction pattern including d-spacings and relative intensities of:

| d-spacing (Å) | Relative Intensity |
|---|---|
| 13.3–13.6 | S |
| 12.0–12.2 | VS |
| 11.5–11.8 | S |
| 10.3–10.6 | S |
| 9.90–10.1 | S |
| 7.60–7.65 | W |
| 6.05–6.15 | W |
| 4.20–4.25 | W |
| 3.85–3.90 | VS |

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, as will occur to one of ordinary skill in the art and having the benefit of this disclosure.

DETAILED DESCRIPTION

Figure 1:
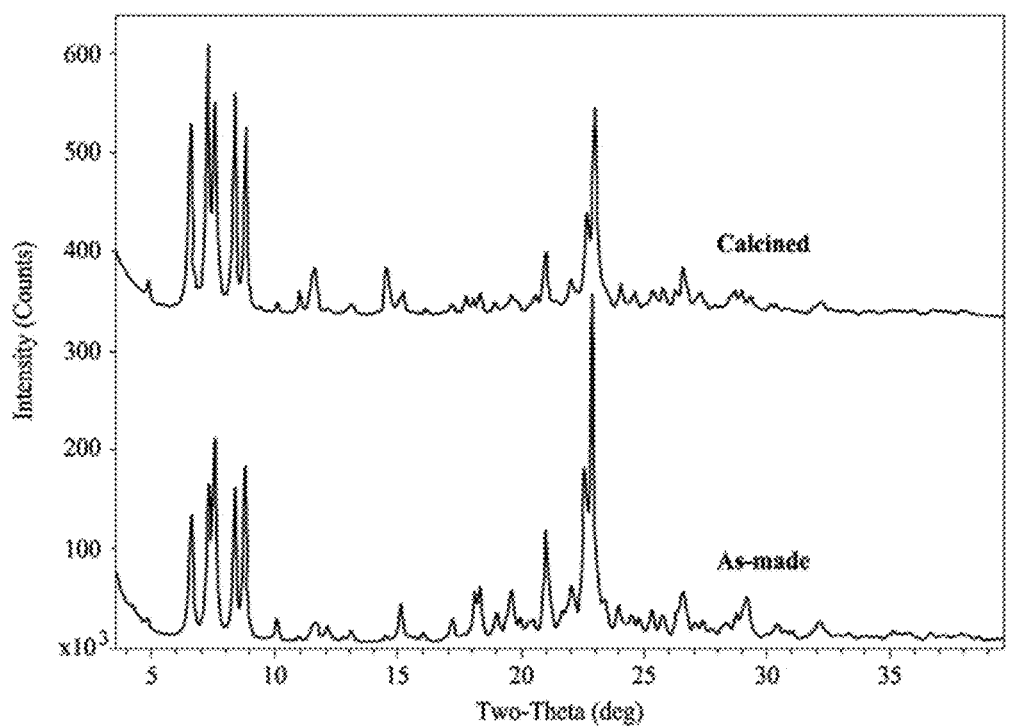
FIG. 1 shows the powder XRD pattern of the material obtained in Example 8.

The present disclosure relates to a zeolite composition (e.g., borosilicates, aluminosilicates, and aluminoborosilicates), methods for preparing such zeolites using quaternary SDAs, and use of said zeolites in organic conversion processes. More specifically, the quaternary SDAs comprise C5 and C6 rings on the chain connecting the ammonium end groups. Such quaternary SDAs are large and, consequently, produce zeolites with large pore sizes. Large pore size zeolites are useful in catalyzed hydrocarbon reactions like propylene and benzene alkylation reactions and aromatic trans alkylation reactions.

Definitions

The term "and/or" as used in a phrase such as "A and/or B" herein is intended to include "A and B," "A or B," "A," and "B."

As used herein, the term "aqueous medium" refers to a liquid comprising predominantly water, particularly about 90 vol. % water or greater. Suitable aqueous media may comprise or consist essentially of water or mixtures of water and a water-miscible organic solvent.

As used herein, the term "trivalent" refers to an atom having a +3 oxidation state.

As used herein, the term "tetravalent" refers to an atom having a +4 oxidation state.

As used herein, the terms "surface directing agent" and "SDA" refer to a templating compound that may promote zeolite synthesis.

As used herein, the terms "calcine," "calcination," and similar variants refer to the process of heating in an oxygen-containing environment (e.g., air or oxygen) above a specified temperature.

As used herein, the term "hydrothermal synthesis" refers to a process in which water and reactants are heated in a closed vessel at a specified temperature for a specified time.

Zeolite EMM-59 Synthesis

As used herein, zeolite EMM-59 is used generally to encompass a borosilicate zeolite EMM-59, an aluminosilicate zeolite EMM-59, and an aluminoborosilicate zeolite EMM-59.

A silicon source along with a boron source and/or an aluminum source can be combined in the presence of a quaternary SDA described herein to form a reaction mixture that is then heated to produce the EMM-59 zeolite.

Examples of silica sources include, but are not limited to, colloidal suspensions of silica, precipitated silica alkali metal silicate, fumed silica, silica hydrogels, hydrated silica, tetraalkyl orthosilicate, and any combination thereof.

Examples of boron sources include, but are not limited to, boric acid, a water-soluble boric acid salt, and any combination thereof.

Examples of aluminum sources include, but are not limited to, aluminum nitrate, aluminum sulfate, sodium aluminate, aluminum oxide, alumina sol, alumina trihydrate, and any combination thereof.

The molar ratio of atomic Si to atomic B in the reaction mixture can range from about 5 to about 50, preferably from about 5 to about 30, and more preferably from about 10 to about 20.

The molar ratio of atomic Si to atomic Al in the reaction mixture can range from about 5 to about 50, preferably from about 5 to about 30, and more preferably from about 10 to about 20.

Generally, quaternary SDAs can be described as compounds of Formula 1:

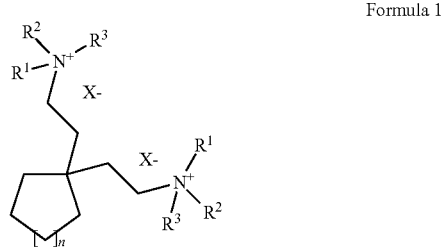

Formula 1 where n can be 1 or 2; $R^1$ and $R^2$ can independently be methyl, ethyl, or $R^1$ and $R^2$ can be joined to form a pyrrolidinium or piperidinium ring with the cationic nitrogen atom of the ammonium end group; and $R^3$ can be methyl or ethyl. Counterions $X^-$ can be $OH^-$, $F^-$, $Cl^-$, $Br^-$, or $I^-$. More specifically, quaternary SDAs can be described as compounds comprising cyclopentyl C5 or cyclohexyl C6 rings on C5 linear chains connecting two ammonium end groups. Example of ammonium end groups include, but are not limited to, N-ethylpyrrolidinium, N-ethylpyperidinium, N,N-diethyl-N-methylammnonium, N-ethyl-N,N-dimethyl-ammnonium, and N,N,N-triethylammnonium. Specific examples of quaternary SDAs include, but are not limited to, Compounds I-VIII, where $X^-$ can be $OH^-$, $F^-$, $Cl^-$, $Br^-$, or $I^-$.

Compound I

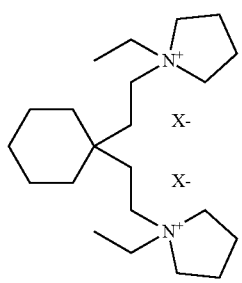

Compound II

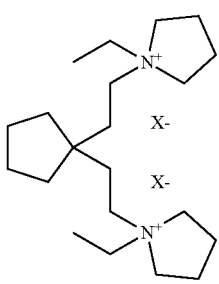

Compound III

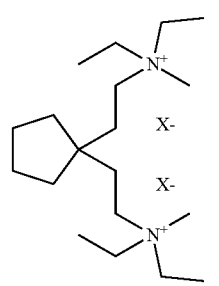

Compound IV

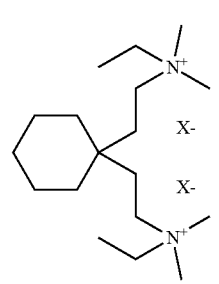

Compound V

Compound VI

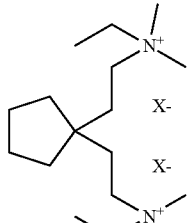

Compound VII

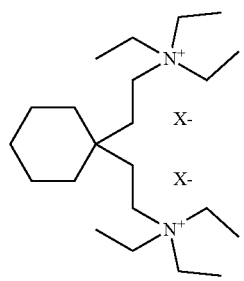

Compound VIII

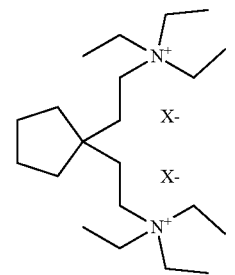

The molar ratio of atomic Si to SDA in the reaction mixture can range from about 1 to about 20, preferably from about 2 to about 15, and more preferably from about 3 to about 10.

In some instances, the reaction mixture may be seeded with a small amount of zeolite EMM-59. The amount of seeds in the reaction mixture can be about 0.1 wt % to about 10 wt % based on the weight of the silica ($SiO_2$) in the reaction mixture, preferably about 0.5 wt % to about 7 wt %, and more preferably about 1 wt % to about 5 wt %. The seeds may be obtained from a previous hydrothermal synthesis of the zeolite EMM-59. Although seeds may facilitate crystallization of the zeolite according to the present disclosure, it is to be appreciated that the zeolite synthesis processes disclosed herein may also proceed without using seeds. When seeds are not employed, slower zeolite crystallization may be observed, in which case longer hydrothermal reaction times may be utilized.

The molar ratio of water to atomic Si in the reaction mixture can range from about 2 to about 80, preferably about 10 to about 65, and more preferably about 15 to about 50.

The zeolite EMM-59 can be prepared under hydrothermal synthesis conditions at a temperature of at least about 75° C. to produce zeolite EMM-59, preferably from about 75° C. to about 200° C., more preferably from about 100° C. to about 185° C., and more preferably from about 150° C. to about 175° C. Suitable hydrothermal synthesis conditions may comprise heating a sealed aqueous solution or suspension of reactants in a vessel, such as an autoclave vessel or 'bomb' in various process configurations. After combining the silicon source, boron and/or aluminum source, and the quaternary SDA with the aqueous medium, a gel may form in some instances. Gel formation may depend upon the amounts of silicon atoms and boron and/or aluminum atoms that are present. Heating of the gel under hydrothermal synthesis conditions may likewise result in zeolite formation according to the disclosure herein.

The syntheses of zeolite EMM-59 can be conducted for a time of at least about 2 hours to produce zeolite EMM-59, preferably about 48 hours to about 50 days, more preferably from about 72 hours to about 40 days, and more preferably from about 7 days to about 30 days. When zeolite EMM-59 seeds are used in the synthesis, the time to crystallization may be less as compared to not using seeds.

The time and temperature of the reaction are interrelated. Typically, lower temperatures require longer reaction times. Further, if a seed is included, then the reaction time, even at lower reaction temperatures, may be reduced.

The produced zeolite EMM-59 of the disclosure preferably has a significantly higher concentration of Si than B and/or Al. As produced from the reaction mixture, the zeolite EMM-59 may have a molar ratio of atomic Si to atomic B and/or a molar ratio of atomic Si to atomic Al, independently, greater than or equal to about 8, preferably from about 12 to about 50, and more preferably from about 15 to about 40.

Isolating the zeolite from the aqueous medium may comprise filtering, decanting, and/or centrifuging the aqueous medium to obtain the zeolite in solid form. Once separated from the aqueous medium, the zeolite may be washed with water or another suitable fluid to remove impurities remaining from the hydrothermal synthesis. Generally, the quaternary SDA remains associated with framework silicate of the zeolite at this juncture and is not removed during washing. Excess quaternary SDA that does not become occluded within the framework silicate of the zeolite during the hydrothermal synthesis is removed during washing at this juncture.

Before or after isolation of the zeolite, a borosilicate zeolite EMM-59 can be treated with an aluminum salt (e.g., aluminum nitrate) at an elevated temperature (e.g., about 75° C. to about 200° C., about 100° C. to about 185° C., or about 150° C. to about 175° C.) for a suitable length of time (e.g., about 2 hours to about 30 days, or about 6 hours to about 7 days, or about 12 hours to about 72 hours) to replace at least a portion of the boron atoms in the borosilicate zeolite EMM-59 with aluminum atoms to produces an aluminoborosilicate zeolite EMM-59 or an aluminosilicate zeolite EMM-59. Therefore, aluminoborosilicate zeolites EMM-59 and aluminosilicate zeolites EMM-59 can be produced directly by the methods described herein or by atom substitution method described herein.

In some instances, at least a portion of the boron in the borosilicate zeolite EMM-59 or at least a portion of the aluminum in the aluminosilicate zeolite EMM-59 can be released or removed from the structure to further increase the Si to B ratio in the borosilicate zeolite EMM-59. This can be achieved by treating the borosilicate zeolite EMM-59 with an acid and/or boiling in hot water.

Examples of acids suitable for treating the zeolite EMM-59 include, but are not limited to, sulfuric acid, hydrochloric acid, acetic acid, nitric acid, and any combination thereof.

The borosilicate zeolite EMM-59 of the present disclosure having been treated to release or remove boron can have a molar ratio of atomic Si to atomic B greater than or equal to about 11. Because almost all of the B can be removed, a molar ratio of atomic Si to atomic B can be infinitely high. The borosilicate zeolite EMM-59 of the present disclosure having been treated to release or remove boron can comprise boron at less than 5 wt % of the borosilicate zeolite EMM-59, or less than 1 wt % of the borosilicate zeolite EMM-59, or less than 0.1 wt % of the borosilicate zeolite EMM-59, or less than 0.01 wt % of the borosilicate Rho zeolite.

The zeolite EMM-59 of the present disclosure may further be calcined in an oxygen-containing environment (e.g., air, oxygen-rich air, or oxygen) to form a calcined zeolite that is free or substantially free of the quaternary SDA. The zeolite EMM-59 (treated after synthesis or as-produced) can be calcined at temperature of from about 350° C. to about 1000° C., preferably from about 400° C. to about 700° C., and more preferably from about 450° C. to about 650° C. Calcination may oxidize the diquaternary SDA into gaseous products, which then exit the pores of the zeolite. The framework of the zeolite EMM-59 is substantially unaffected by the calcination process, as evidenced by characteristic scattering angles of the powder x-ray diffraction spectrum remaining largely unchanged between the pre-calcination zeolite and the post-calcination zeolite. Suitable calcination times may range from about 1 hour to about 48 hours, or even longer.

The zeolite EMM-59 (treated after synthesis or as-produced) can have an average crystal dimension of from about 0.02 microns to about 25 microns, preferably from about 0.04 micron to about 1 microns. Particle size can be determined by imaging the crystals with scanning electron microscopy and averaging the diameter of at least 100 crystals. The crystals have a facetted shape. Therefore, the diameter is defined as the largest distance passing from one side to the other through the center of the crystal.

The zeolite EMM-59 (treated after synthesis or as-produced) can have surface area of from about 500 $m^2/g$ to about 1000 $m^2/g$, preferably from about 600 $m^2/g$ to about 800 $m^2/g$, and more preferably from about 640 $m^2/g$ to about 720 $m^2/g$. Surface area is determined using Brunauer, Emmett and Teller (BET) analysis with nitrogen adsorption (ASTM D4365-13).

The zeolite EMM-59 (treated after synthesis or as-produced) can have micropore volume of from about 0.15 $cm^3/g$ to about 0.50 $cm^3/g$, preferably from about 0.20 $cm^3/g$ to about 0.40 $cm^3/g$, and more preferably from about 0.22 $cm^3/g$ to about 0.30 $cm^3/g$. Micropore volume is determined via nitrogen adsorption by ASTM D4365-13.

The zeolite EMM-59 (treated after synthesis or as-produced) can have a framework symmetry of C2/m and unit cell measurements according to Table 1.

TABLE 1

|  | Broad Range | Preferred Range |
|---|---|---|
| a (Å) | 3.0 to 5.0 | 3.5 to 4.5 |
| b (Å) | 19 to 22 | 20.1 to 21.1 |
| c (Å) | 15 to 17 | 15.5 to 16.5 |
| β (°) | 96 to 99 | 97 to 98 |

The as-synthesized and treated (e.g., calcined or acid treated) borosilicate zeolite EMM-59 can have characteristic X-ray diffraction (XRD) patterns, the essential (most intense) reflection lines of which may be represented in Table 2 (as synthesized form) and Table 3 (calcined form). Variations can occur as a function of the specific composition and SDA used in synthesis. For this reason, the relative integrated intensities (qualified as VS=very strong, S=strong, SM=medium strong, W=weak) and d-spacings are represented as ranges in Tables 2 and 3. The aluminosilicate and aluminoborosilicate zeolites have characteristic X-ray diffraction (XRD) patterns within the ranges of to those shown in Table 3.

TABLE 2

| d-spacing (Å) | Relative Intensity |
|---|---|
| 13.2-13-5 | SM |
| 11.9-12.2 | S |
| 11.5-11.8 | S |
| 10.3-10.6 | SM |
| 9.95-10.2 | S |
| 4.20-4.27 | SM |
| 3.92-3.96 | SM |
| 3.87-3.92 | VS |
| 3.04-3.08 | W |

TABLE 3

| d-spacing (Å) | Relative Intensity |
|---|---|
| 13.3-13-6 | S |
| 12.0-12.2 | VS |
| 11.5-11.8 | S |
| 10.3-10.6 | S |
| 9.90-10.1 | S |
| 7.60-7.65 | W |
| 6.05-6.15 | W |
| 4.20-4.25 | W |
| 3.85-3.90 | VS |

Applications

As in the case of many catalysts used in organic compound (hydrocarbon) conversion processes, it may be desirable to incorporate the zeolite EMM-59 with another material resistant to the temperatures and other conditions employed in organic conversion processes. Such materials can include active and inactive materials and synthetic or naturally occurring zeolites, as well as inorganic materials such as clays, silica, and/or metal oxides such as alumina. The latter may be either naturally occurring or in the form of gelatinous precipitates or gels, including mixtures of silica and metal oxides. Use of a material in conjunction with the zeolite EMM-59 (i.e., combined therewith and/or present during synthesis of the new crystal, which is active) can tend to change the conversion and/or selectivity of the catalyst in certain organic conversion processes. Inactive materials can suitably serve as diluents to control the amount of conversion in a given process so that products can be obtained in an economic and orderly manner without employing other (more costly) means for controlling the rate of reaction. These materials may be incorporated into naturally occurring clays (e.g., bentonite and kaolin) to improve the crush strength of the catalyst under commercial operating conditions. Said materials (i.e., clays, oxides, etc.) can function as binders for the catalyst. It can be desirable to provide a catalyst having good crush strength, because in commercial use it can be desirable to prevent the catalyst from breaking down into powder-like materials (attrition). These clay and/or oxide binders have been employed normally only for the purpose of improving the crush strength of the catalyst.

Naturally occurring clays which can be composited with the zeolite EMM-59 can include, without limitation, the montmorillonite and kaolin family, which families include the subbentonites, and the kaolins commonly known as Dixie, McNamee, Georgia, and Florida clays, or others in which the main mineral constituent is halloysite, kaolinite, dickite, nacrite, or anauxite. Such clays can be used in the raw state as originally mined or initially subjected to calcination, acid treatment, or chemical modification. Binders useful for compositing with the zeolite EMM-59 can additionally or alternatively include inorganic oxides, such as silica, zirconia, titania, magnesia, beryllia, alumina, and mixtures thereof.

Alternatively or in addition to the foregoing materials, the zeolite EMM-59 can be composited with a porous matrix material such as silica-alumina, silica-magnesia, silica-zirconia, silica-thoria, silica-beryllia, silica-titania, and/or one or more ternary compositions such as silica-alumina-thoria, silica-alumina-zirconia silica-alumina-magnesia, and silica-magnesia-zirconia.

The relative proportions of zeolite EMM-59 and inorganic oxide matrix may vary widely, with the zeolite EMM-59 content ranging from about 1 wt % to about 90 wt %, and, more usually, particularly when the composite is prepared in the form of beads, in the range of about 2 wt % to about 80 wt % of the composite. An exemplary matrix content range can include from about wt % to about 50 wt %.

Numerical ranges used herein include the numbers recited in the range. For example, the numerical range "from 1 wt % to 10 wt %" includes 1 wt % and 10 wt % within the recited range.

EXAMPLE EMBODIMENTS

A first example embodiment of the present invention is a method comprising: heating an aqueous reaction mixture comprising (a) a silicon source and (b) a boron source and/or an aluminum source in the presence of a structure directing agent to a temperature of at least 75° C. to produce a zeolite, wherein the structure directing agent is represented by Formula 1, wherein n is or 2; each of $R^1$ and $R^2$ is independently methyl or ethyl, or $R^1$ and $R^2$ are joined to form a pyrrolidinium or piperidinium ring; $R^3$ is methyl or ethyl; and $X^-$ is $OH^-$, $F^-$, $Cl^-$, $Br^-$, or $I^-$. This example embodiment can include one or more of the following: Element 1: wherein the structure directing agent is selected from any one of Compounds I-VIII, or a mixture of two or more of Compounds I-VIII; Element 2: wherein the aqueous reaction mixture has a molar ratio of atomic Si to the structure directing agent of about 1 to about 20; Element 3: wherein the aqueous reaction mixture has a molar ratio of water to atomic Si of about 2 to about 80; Element 4: wherein the aqueous reaction mixture has a molar ratio of atomic Si to atomic B of about 12 to about 50; Element 5: wherein the aqueous reaction mixture has a molar ratio of atomic Si to atomic Al of about 12 to about 50; Element 6: wherein a Si source in the aqueous reaction mixture is selected from the group consisting of: a colloidal suspension of silica, a precipitated silica alkali metal silicate, fumed silica, silica hydrogels, hydrated silica, tetraalkyl orthosilicate, and any combination thereof; Element 7: wherein a B source in the aqueous reaction mixture is selected from the group consisting of: boric acid, a water-soluble boric acid salt, and any combination thereof; Element 8: wherein heating occurs for 2 hours to 50 days; Element 9: wherein the aqueous reaction mixture further comprises zeolite seeds; Element 10: wherein the zeolite is a borosilicate zeolite, and wherein, in an as-synthesized form, the borosilicate zeolite has an X-ray diffraction pattern including d-spacings (d(Å)) and relative intensities shown in Table 2; Element 11: further comprising: calcining the zeolite at 350° C. to about 1000° C. to produce a calcined zeolite; and Element 12: wherein the zeolite is a borosilicate zeolite, and wherein the calcined borosilicate zeolite has an X-ray diffraction pattern including d-spacings (d(Å)) and relative intensities shown in Table 3. Example combinations include, but are not limited to, two or more of Elements 1-11; Element 11 in combination with Element 12; one or more of Elements 1-10 in combination with Element 11 and optionally in further combination with Element 12.

Another example embodiment is a zeolite produced by the method of the first embodiment optionally including one or more of Element 1-11, or optionally including one or more of Elements 1-10 in combination with Element 11 and optionally in further combination with Element 12.

Yet another example embodiment is a composition comprising a borosilicate zeolite, an aluminosilicate zeolite, or an aluminoborosilicate zeolite having a framework symmetry of C2/m and a unit cell with measurements of a of 3.5 Å to 4.5 Å, b of 20.1 Å to 21.1 Å, c of 15.5 to 16.5 Å, and β of 97° to 98°.

Another example embodiment is a composition comprising a borosilicate zeolite having a micropore volume of about 0.24 cm³/g to about 0.28 cm³/g and having an X-ray diffraction pattern including d-spacings and relative intensities shown in Table 2.

Yet another example embodiment is a composition comprising a borosilicate zeolite, an aluminosilicate zeolite, or an aluminoborosilicate zeolite having a micropore volume of about 0.24 cm³/g to about 0.28 cm³/g and having an X-ray diffraction pattern including d-spacings and relative intensities shown in Table 3.

To facilitate a better understanding of the embodiments described herein, the following examples of various representative embodiments are given. In no way should the following examples be read to limit, or to define, the scope of the present disclosure.

EXAMPLES

Example 1: Synthesis of 1,1'-(cyclohexane-1,1-diylbis (ethane-2,1-diyl))bis(1-ethylpyrrolidin-1-ium) Hydroxide (Compound I). 1,1'-(cyclohexane-1,1-diylbis(ethane-2,1-diyl))bis(1-ethylpyrrolidin-1-ium) hydroxide was synthesized in four steps from 3-oxaspiro-[5,5]-undecane-2,4-dione as follows. The 1,1'-(cyclohexane-1,1-diylbis(ethane-2,1-diyl))bis(1-ethylpyrrolidin-1-ium) hydroxide was then used as a directing agent in the zeolite syntheses outlined further below.

Synthesis of 2,2'-(cyclohexane-1,1-diyl)bis(1-(pyrrolidin-1-yl)ethan-1-one)

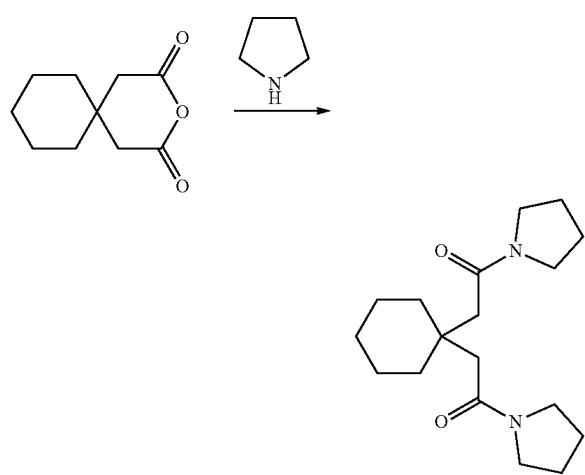

To a flame dried 500 mL round bottom flask with stir bar was added 100 mL of anhydrous tetrahydrofuran. 3-oxaspiro-[5,5]-undecane-2,4-dione (9.11 g, 50.0 mmol) was added to the flask and the flask was purged with nitrogen. Pyrrolidine (10.7 g, 150.0 mmol, 3 eq) was added via syringe and the reaction mixture was refluxed at 95° C. for 1 hour. The heat was removed and the reaction cooled to room temperature. Pyridine (13.1 g, 165 mmol, 3.3 eq) was added via syringe and the reaction mixture was cooled to 0° C. Propylphosphonic anhydride solution (50% by wt in EtOAc, 63.64 g, 100 mmol, 2 eq) was slowly poured in from a beaker (anhydride solution is very viscous) and reaction stirred under nitrogen in the ice bath overnight (ice allowed to melt). 170 mL of 10% aqueous HCl was added to the reaction mixture. This solution was stirred vigorously for 24 hours. The reaction mixture was transferred to a 500 mL separator funnel and extracted 3 times with 75 mL of methylene chloride. Organics were dried with sodium sulfate, gravity filtered into a pre-weighed round bottom, and solvent was removed under vacuum to yield an oil (15.32 g, 50.0 mmol, 100% yield). The product was pure enough for the next step without further purification. The product of this first step had the expected $^1$H NMR spectra. $^1$H NMR (400 MHz, CDCl$_3$): δ ppm: 3.48 (t, 4H), 3.40 (t, 4H), 2.60 (s, 4H), 1.90 (m, 4H), 1.80 (m, 4H), 1.68 (m, 4H), 1.43 (m, 6H).

Synthesis of 1,1'-(cyclohexane-1,1-diylbis(ethane-2,1-diyl))dipyrrolidine

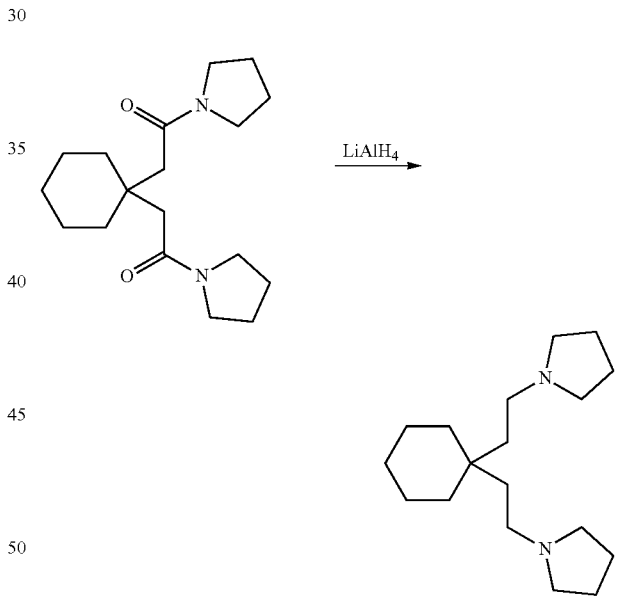

To a flame dried 1000 mL 3 necked round bottom flask with stir bar was added 400 mL of anhydrous tetrahydrofuran via cannula. Slowly, lithium aluminum hydride powder (4.74 g, 125 mmol, 2.5 eq) was added to the vigorously stirring solution. Separately, the diamide obtained from the first step of this synthesis (15.32 g, 50.0 mmol) was dissolved in 100 mL of anhydrous tetrahydrofuran and transferred to a flame dried liquid addition funnel. The diamide solution was slowly dripped into the lithium aluminum hydride suspension. Once the diamide solution was completely added, the rubber stoppers were replaced with glass stoppers and the reaction refluxed under nitrogen for 2 hours before stirring at room temperature overnight. The reaction vessel was uncapped and 4.74 mL of deionized water was added to a liquid addition funnel and added drop-wise to the stirring reaction mixture. Following this, 4.74 mL of 10% aqueous NaOH was added to the liquid addition funnel and added drop-wise to the stirring mixture. Next, 14.22 mL of deionized water was dripped into the stirring mixture and the mixture was stirred at room temperature for 1 hour. The reaction mixture was filtered through a celite pad and the solid aluminum hydroxide salts were washed 3 times with 50 mL of diethyl ether. The ether filtrate was dried with sodium sulfate, gravity filtered into a pre-weighed round bottom flask, and solvent was removed under vacuum to yield a colorless oil (12.79 g, 46.0 mmol, 92% yield). The product was pure enough for the next step without further purification. The product of this second step had the expected $^1$H NMR spectra. $^1$H NMR (400 MHZ, CDCl$_3$): δ ppm: 2.49 (m, 8H), 2.39 (m, 4H), 1.75 (m, 8H), 1.49 (m, 4H), 1.35-1.45 (m, 6H), 1.29 (t, 4H).

Synthesis of 1,1'-(cyclohexane-1,1-diylbis(ethane-2,1-diyl))bis(1-ethylpyrrolidin-1-ium) iodide

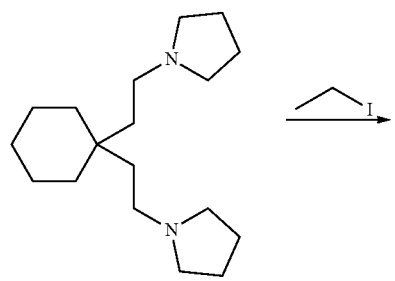

The diamine obtained from the second step of this synthesis (12.79 g, 46.0 mmol) was dissolved in 100 mL of acetone in a 250 mL round bottom flask with stir bar. Iodoethane (35.96 g, 230.66 mmol, 5 eq) was added via syringe and the reaction stirred at room temperature while loosely capped for 72 hours. The very cloudy reaction mixture was poured over a medium grade frit and the white solid was washed 3 times with 20 mL of acetone and dried to afford pure product (21.73 g, 36.8 mmol, 80% yield). The product of this third step had the expected $^1$H NMR spectra. $^1$H NMR (400 MHZ, D$_2$O): δ ppm: 3.25-3.45 (m, 8H), 3.20 (q, 4H), 3.10 (m, 4H), 2.00 (m, 8H), 1.58 (m, 4H), 1.30 (m, 4H), 1.22 (m, 6H), 0.80 (t, 6H).

Synthesis of 1,1'-(cyclohexane-1,1-diylbis(ethane-2,1-diyl))bis(1-ethylpyrrolidin-1-ium) hydroxide

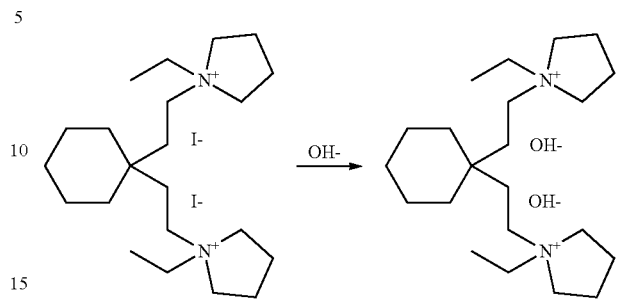

1,1'-(cyclohexane-1,1-diylbis(ethane-2,1-diyl))bis(1-ethylpyrrolidin-1-ium) iodide was converted to its hydroxide form by dissolving it in water and adding it to 700 mL of Dowex LC NG hydroxide exchange resin. After contacting the exchange resin overnight, the resin was removed by filtration and washed with deionized water. The aqueous fractions were then combined and concentrated under reduced pressure at about 60° C. The hydroxide concentration of this aqueous solution was 14.9 wt % as determined by titration with a standard solution of 0.1 N HCl.

Example 2: Synthesis of 1,1'-(cyclopentane-1,1-diylbis(ethane-2,1-diyl))bis(1-ethylpyrrolidin-1-ium) Hydroxide (Compound II). 1,1'-(cyclopentane-1,1-diylbis(ethane-2,1-diyl))bis(1-ethylpyrrolidin-1-ium) hydroxide was synthesized in four steps from 3,3-tetramethyleneglutaric anhydride as follows. The 1,1'-(cyclopentane-1,1-diylbis(ethane-2,1-diyl))bis(1-ethylpyrrolidin-1-ium) hydroxide was then used as a directing agent in the zeolite syntheses outlined further below.

Synthesis of 2,2'-(cyclopentane-1,1-diyl)bis(1-(pyrrolidin-1-yl)ethan-1-one)

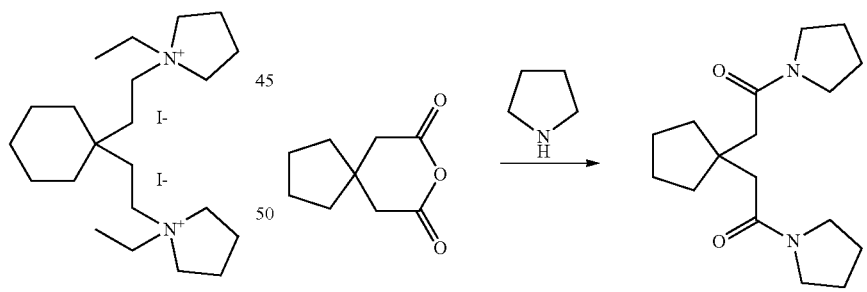

To a flame dried 500 mL round bottom flask with stir bar was added 100 mL of anhydrous tetrahydrofuran. 3,3-tetramethyleneglutaric anhydride (10.0 g, 59.5 mmol) was added to the flask and the flask was purged with nitrogen. Pyrrolidine (12.69 g, 178.4 mmol, 3 eq) was added via syringe and the reaction mixture was refluxed at 95° C. for 1 hour. The heat was removed and the reaction cooled to room temperature. Pyridine (15.53 g, 196.4 mmol, 3.3 eq) was added via syringe and the reaction mixture was cooled to 0° C. Propylphosphonic anhydride solution (50% by wt in EtOAc, 75.73 g, 119.0 mmol, 2 eq) was slowly poured in from a beaker (anhydride solution is very viscous) and reaction stirred under nitrogen in the ice bath overnight (ice allowed to melt). 200 mL of 10% aqueous HCl was added to the reaction mixture. This solution was stirred vigorously for 24 hours. The reaction mixture was transferred to a 500 mL separatory funnel and extracted 3 times with 75 mL of methylene chloride. Organics were dried with sodium sulfate, gravity filtered into a pre-weighed round bottom, and solvent was removed under vacuum to yield an oil (16.87 g, 57.7 mmol, 97% yield). The product was pure enough for the next step without further purification. The product of this first step had the expected $^1$H NMR spectra. $^1$H NMR (400 MHZ, CDCl$_3$): δ ppm: 3.30 (m, 8H), 2.50 (s, 4H), 1.78 (m, 4H), 1.68 (m, 4H), 1.60 (m, 4H), 1.47 (m, 4H).

Synthesis of 1,1'-(cyclopentane-1,1-diylbis(ethane-2,1-diyl))dipyrrolidine

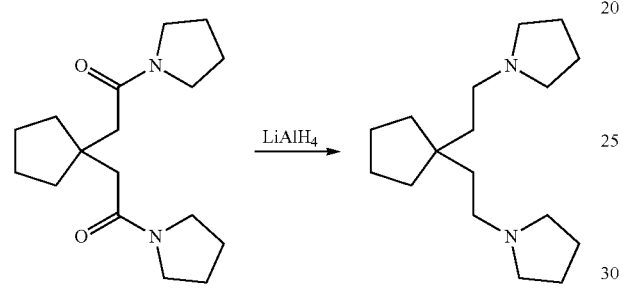

To a flame dried 1000 mL 3 necked round bottom flask with stir bar was added 400 mL of anhydrous tetrahydrofuran. Slowly, lithium aluminum hydride powder (5.00 g, 131.8 mmol, 2.5 eq) was added to the stirring solution. Separately, the diamide obtained from the first step of this synthesis (15.40 g, 52.70 mmol) was dissolved in 100 mL of anhydrous tetrahydrofuran and transferred to a flame dried liquid addition funnel. The diamide solution was slowly dripped into the lithium aluminum hydride suspension. Once the diamide solution was completely added, the rubber stoppers were replaced with glass stoppers and the reaction mixture refluxed under nitrogen for 2 hours before stirring at room temperature overnight. The reaction vessel was uncapped and 5.00 mL of deionized water was added to a liquid addition funnel and added dropwise to the stirring reaction mixture. Following this, 5.00 mL of 10% aqueous NaOH was added to the liquid addition funnel and added dropwise to the stirring mixture. Next, 15.00 mL of deionized water was dripped into the stirring mixture and the mixture was stirred at room temperature for 1 hour. The reaction mixture was filtered through a celite pad and the solid aluminum hydroxide salts were washed 3 times with 50 mL of diethyl ether. The filtrate was dried with sodium sulfate, gravity filtered into a pre-weighed round bottom flask, and solvent was removed under vacuum to yield a colorless oil (12.54 g, 47.43 mmol, 90% yield). The product was pure enough for the next step without further purification. The product of this second step had the expected $^1$H NMR spectra. $^1$H NMR (400 MHZ, CDCl$_3$): δ ppm: 2.48 (m, 8H), 2.43 (m, 4H), 1.77 (m, 8H), 1.58 (m, 4H), 1.50 (m, 4H), 1.40 (m, 4H).

Synthesis of 1,1'-(cyclopentane-1,1-diylbis(ethane-2,1-diyl))bis(1-ethylpyrrolidin-1-ium) iodide

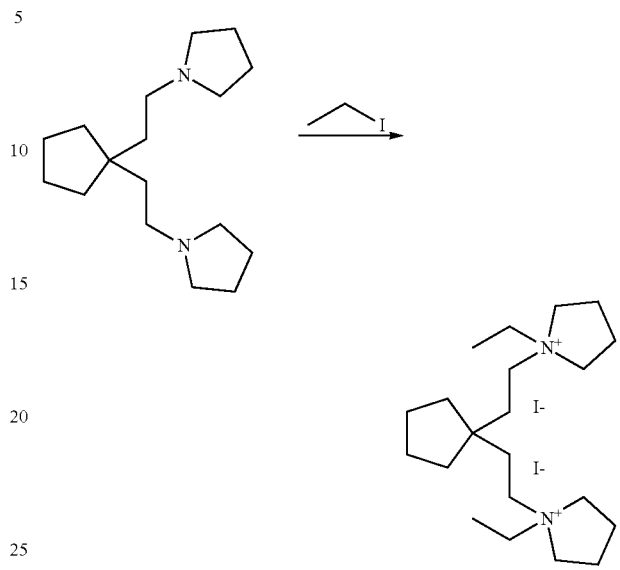

The diamine obtained from the second step of this synthesis (12.54 g, 47.43 mmol) was dissolved in 100 mL of acetone in a 250 mL round bottom flask with stir bar. Iodoethane (36.99 g, 237.15 mmol, 5 eq) was added via syringe and the reaction stirred at room temperature while loosely capped for 72 hours. The very cloudy reaction mixture was filtered through a medium frit funnel and the resulting white solid was washed 3 times with 20 mL of acetone and dried to afford pure product (21.31 g, 37.0 mmol, 78% yield). The product of this third step had the expected $^1$H NMR spectra. $^1$H NMR (400 MHZ, D$_2$O): δ ppm: 3.25-3.40 (m, 8H), 3.05-3.20 (m, 8H), 2.00 (m, 8H), 1.60 (m, 4H), 1.48 (m, 4H), 1.35 (m, 4H), 0.80 (t, 6H).

Synthesis of 1,1'-(cyclopentane-1,1-diylbis(ethane-2,1-diyl))bis(1-ethylpyrrolidin-1-ium) hydroxide

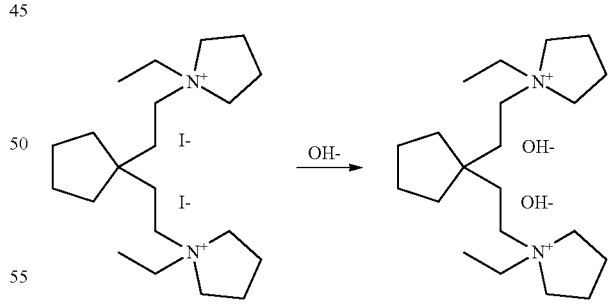

1,1'-(cyclopentane-1,1-diylbis(ethane-2,1-diyl))bis(1-ethylpyrrolidin-1-ium)iodide was converted to its hydroxide form by dissolving it in water and adding it to 700 mL of Dowex LC NG hydroxide exchange resin. After contacting the exchange resin overnight, the resin was removed by filtration and washed with deionized water. The aqueous fractions were then combined and concentrated under reduced pressure at about 60° C. The hydroxide concentration of this aqueous solution was 16.6 wt % as determined by titration with a standard solution of 0.1 N HCl.

Example 3: Synthesis of 2,2'-(cyclohexane-1,1-diyl)bis(N,N-diethyl-N-methylethane-1-aminium) iodide (Compound III). 2,2'-(cyclohexane-1,1-diyl)bis(N,N-diethyl-N-methylethane-1-aminium) iodide was synthesized in three steps from 3-oxaspiro-[5,5]-undecane-2,4-dione as follows. The 1,1'-(cyclohexane-1,1-diylbis(ethane-2,1-diyl))bis(1-ethylpyrrolidin-1-ium) iodide was then used as a directing agent in the zeolite syntheses outlined further below.

1-(diethylamino)-2-{1-[2-(diethylamino)-2-oxoethyl]cyclohexyl}-1-ethanone

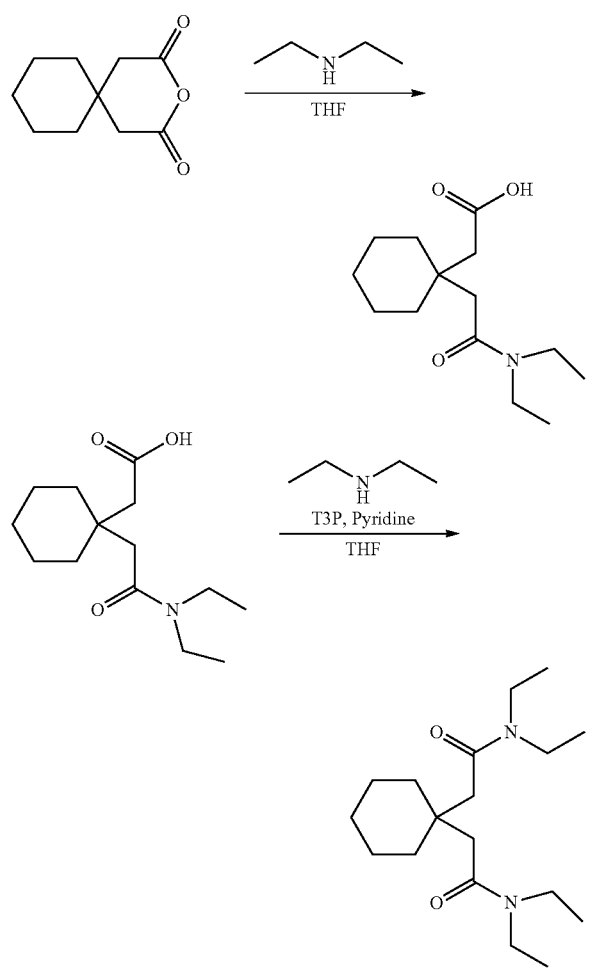

3-oxaspiro-[5,5]-undecane-2,4-dione (10.93 g, 60 mmol, 1 eq) was dissolved in anhydrous THF (150 mL). Diethylamine (13.17 g, 180 mmol, 3 eq) was added to the reaction mixture via syringe. The reaction mixture was stirred, and refluxed at 80° C. for 1.5 hours and then allowed to cool to room temperature. The carboxylic acid intermediate was not isolated and was carried on directly to the next step. Pyridine (12.43 g, 457.1 mmol, 3.3 eq) was added to the solution and the mixture was cooled to 0° C. Propylphosphonic anhydride (T3P) (30.29 g, 95.2 mmol, 2 eq) was added slowly to the mixture and the reaction was allowed to warm to room temperature while stirring overnight. The reaction was then cooled back to 0° C. and 0.5 M HCl (180 mL) was added. The mixture was allowed to stir for 6.5 hours. The reaction mixture was transferred to a 500 mL separatory funnel and extracted with 100 mL of DCM three times. The organic layers were combined and dried with potassium carbonate. The solvent was removed under vacuum to afford 1-(diethylamino)-2-{1-[2-(diethylamino)-2-oxoethyl]cyclohexyl}-1-ethanone as a yellow oil (13.85 g, 44.6 mmol, 94%). The product of this first step had the expected $^1$H NMR spectra. $^1$H NMR (400 MHZ, CDCl$_3$): δ ppm: 3.45 (m, 8H), 2.6 (s, 4H), 1.7 (m, 4H), 1.48 (m, 6H), 1.17 (t, 6H), 1.08 (t, 6H).

Synthesis of 1-(diethylamino)-2-{1-[2-(diethylamino)ethyl]cyclohexyl}ethane

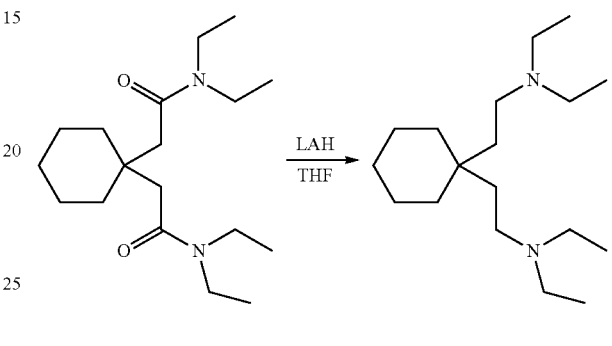

Lithium aluminum hydride (3.72 g, 98.1 mmol, 2.2 eq) was dissolved in 250 mL of anhydrous THF in a flame-dried 3-necked 1 L round bottom flask. Diamide 1-(diethylamino)-2-{1-[2-(diethylamino)-2-oxoethyl]cyclohexyl}-1-ethanone (13.85 g, 44.6 mmol, 1 eq) was dissolved in 200 mL of anhydrous THF then dripped into the LiAlH$_4$/THF mixture via a dropping funnel. After the addition of diamide was complete the reaction was heated to 80° C. and refluxed for 1.5 hours and then left to stir and cool to room temperature overnight. The reaction was then quenched with the 1:1:3 method (1 mL of water, 1 mL of 10% aq. NaOH, 3 mL of water for each gram of LiAlH$_4$ used). The reaction mixture was filtered through a pad of celite on a medium fritted disk funnel and the celite was washed with diethyl ether. The organic filtrate was dried with potassium carbonate and the solvent was removed under vacuum to afford 1-(Diethylamino)-2-{1-[2-(diethylamino)ethyl]cyclohexyl}ethane as a light yellow oil (9.43 g, 33.4 mmol, 75%). The product of this second step had the expected $^1$H NMR spectra. $^1$H NMR (400 MHZ, CDCl$_3$): δ ppm: 2.51 (q, 8H), 2.40 (m, 4H), 1.42 (m, 10H), 1.29 (m, 4H), 1.03 (t, 12H).

Synthesis of 2,2'-(cyclohexane-1,1-diyl)bis(N,N-diethyl-N-methylethan-1-aminium) iodide

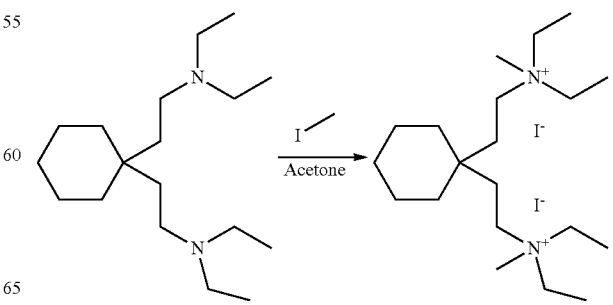

The diamine obtained from the second step of this synthesis (12.79 g, 46.0 mmol) was dissolved in 100 mL of acetone in a 500 mL round bottom flask with stir bar. Methyl iodide (23.7 g, 167 mmol, 5 eq) was added to the reaction via a syringe. The reaction was allowed to stir under nitrogen at room temperature for 4 days. The white precipitate was recovered by filtration through a fritted disk funnel and washed with acetone several times to afford 2,2'-(cyclohexane-1,1-diyl)bis(N,N-diethyl-N-methylethan-1-aminium) iodide as a white powder (15.6 g, 27.54 mmol, 83%). The product of this third step had the expected $^1$H NMR spectra. $^1$H NMR (400 MHZ, D$_2$O): δ ppm: 3.20 (q, 8H), 3.1 (m, 4H), 2.80 (s, 6H), 2.04 (m, 4H), 1.29 (m, 10H, broad), 1.17 (t, 12H). This iodide product was converted to its hydroxide form similarly than Examples 1 and 2.

Example 4: Synthesis of 2,2'-(cyclohexane-1,1-diyl)bis (N-ethyl-N,N-dimethylethane-1-aminium) iodide (Compound V). 2,2'-(cyclohexane-1,1-diyl)bis(N-ethyl-N,N-dimethylethane-1-aminium) iodide was synthesized in four steps from 3-oxaspiro-[5,5]-undecane-2,4-dione as follows. The 2,2'-(cyclohexane-1,1-diyl)bis(N-ethyl-N,N-dimethylethane-1-aminium) iodide was then used as a directing agent in the zeolite syntheses outlined further below.

1-(Dimethylamino)-2-{1-[2-(dimethylamino)-2-oxoethyl]cyclohexyl}-1-ethanone

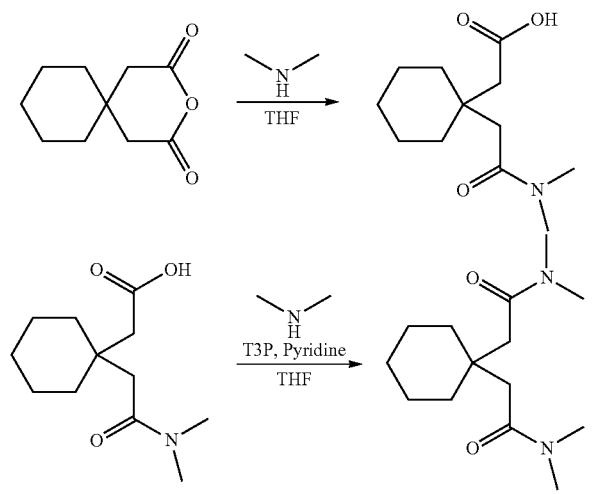

3-oxaspiro-[5,5]-undecane-2,4-dione (9.11 g, 50 mmol, 1 eq) was dissolved in anhydrous THF (40 mL). Dimethylamine (2.0 M in THF) (75 mL, 150 mmol, 3 eq) was added to the reaction mixture via syringe. The reaction was stirred, and refluxed at 95° C. for 1.5 hours, and then allowed to cool to room temperature. The carboxylic acid intermediate was not isolated and was carried on directly to next step. Pyridine (13.1 g, 165 mmol, 3.3 eq) was added to the solution then cooled to 0° C. Propylphosphonic anhydride (T3P) (31.82 g, 100 mmol, 2 eq) was added slowly to the mixture and the reaction was allowed to warm to room temperature while stirring overnight. The reaction was then cooled back to 0° C. and 0.5 M HCl (170 mL) was added. The mixture was stirred for 6.5 hours. The reaction mixture was transferred to a 500 mL separatory funnel and extracted with 75 mL of DCM three times. The organic layers were combined and dried with potassium carbonate. The solvent was removed under vacuum to afford 1-(dimethylamino)-2-{1-[2-(dimethylamino)-2-oxoethyl]cyclohexyl}-1-ethanone as a yellow oil (12.7 g, 49.93 mmol, 100%). The product of this first step had the expected $^1$H NMR spectra. $^1$H NMR (400 MHZ, CDCl$_3$): δ ppm: 3.04 (s, 6H), 2.90 (s, 6H), 2.65 (s, 4H), 1.66 (m, 4H), 1.43 (m, 6H).

Synthesis of 1-(dimethylamino)-2-{1-[2-(dimethylamino)ethyl]cyclohexyl}ethane

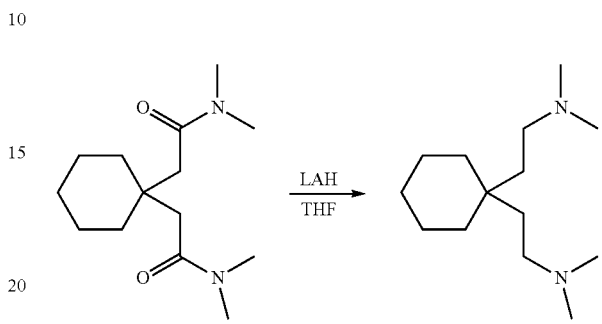

Lithium aluminum hydride (4.36 g, 115 mmol, 2.3 eq) was dissolved in 200 mL of anhydrous THF in a flame-dried 3-necked 1 L round bottom flask. Diamide 1-(dimethylamino)-2-{1-[2-(dimethylamino)-2-oxoethyl]cyclohexyl}-1-ethanone (12.7 g, 50 mmol, 1 eq) was dissolved in 200 mL of anhydrous THF then dripped slowly into the LiAlH$_4$/THF solution via a flame-dried dropping funnel. After all of the diamide was added, the reaction mixture was heated to 70° C., refluxed for 3 hours then left to stir and cool to room temperature overnight. The reaction was quenched with the 1:1:3 method (1 mL of water, 1 mL of 10% aq. NaOH, 3 mL of water for each gram of LiAlH$_4$ used). The reaction was filtered through a celite pad on a medium fritted disk funnel and the pad was rinsed with diethyl ether. The organic filtrate was dried with sodium sulfate and the solvent was removed under vacuum to afford 1-(dimethylamino)-2-{1-[2-(dimethylamino)ethyl]cyclohexyl}ethane as a clear oil (10.4 g, 45.93 mmol, 92%). The product of this second step had the expected $^1$H NMR spectra. $^1$H NMR (400 MHZ, CDCl$_3$): δ ppm: 2.17-2.24 (s, 16H), 1.43 (m, 10H), 1.28 (t, 4H).

Synthesis of 2,2'-(cyclohexane-1,1-diyl)bis(N-ethyl-N,N-dimethylethane-1-aminium) iodide

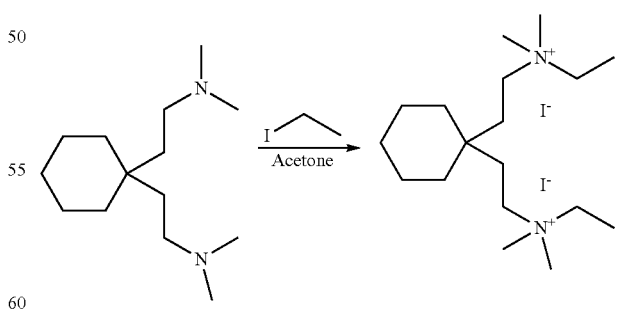

The diamine obtained from the second step of this synthesis (10.4 g, 46 mmol, 1 eq) was dissolved in 125 mL of acetone in a 500 mL round-bottom flask charged with a stir bar. Ethyl iodide (35.8 g, 230 mmol, 5 eq) was added to the reaction via a syringe. The reaction was stirred under nitrogen for 4 days at room temperature. The white precipitate was recovered by filtration through a fritted disk funnel and washed with acetone several times to afford 2,2'-(cyclohexane-1,1-diyl)bis(N-ethyl-N,N-dimethylethane-1-aminium) iodide as a white powder. (21.94 g, 40.75 mmol, 89%). The product of this third step had the expected $^1$H NMR spectra. $^1$H NMR (400 MHZ, D$_2$O): δ ppm: 3.24 (q, 4H), 3.14 (m, 4H), 2.89 (s, 12H), 1.60 (m, 4H), 1.33 (m, 4H), 1.23 (m, 6H), 1.17 (t, 6H). This iodide product was converted to its hydroxide form similarly than Examples 1 and 2.

Example 5: Synthesis of 2,2'-(cyclopentane-1,1-diyl)bis(N,N,N-triethylethan-1-aminium) iodide (Compound VIII). 2,2'-(cyclopentane-1,1-diyl)bis(N,N,N-triethylethan-1-aminium) iodide was synthesized in three steps from 3,3-tetramethylene glutaric anhydride as follows. The 2,2'-(cyclopentane-1,1-diyl)bis(N,N,N-triethylethan-1-aminium) iodide was then used as a directing agent in the zeolite syntheses outlined further below.

1-(Diethylamino)-2-{1-[2-(diethylamino)-2-oxoethyl]cyclopentyl}-1-ethanone

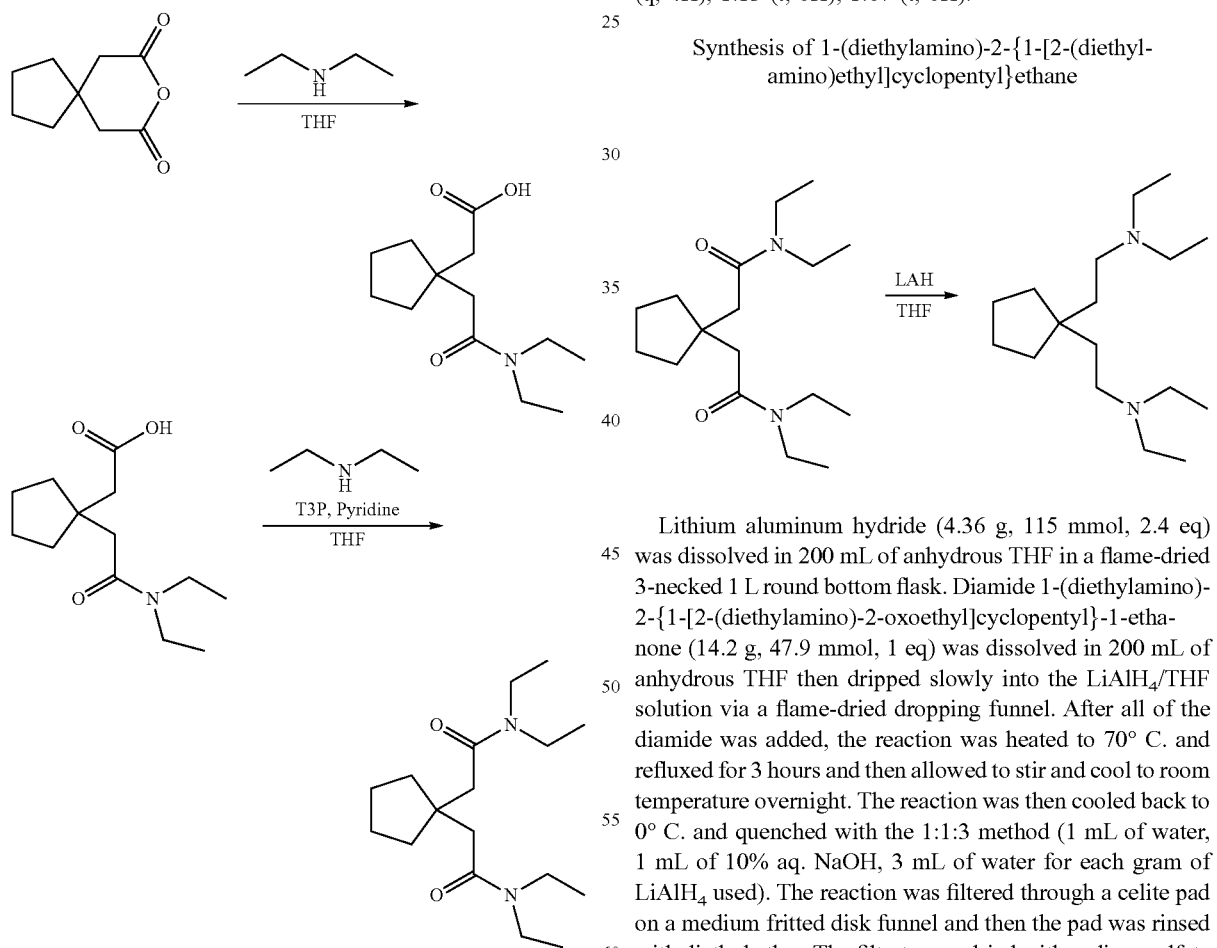

3,3-tetramethylene glutaric anhydride (5.0 g, 29.7 mmol, 1 eq) was dissolved in 50 mL of anhydrous THF in a flame-dried 200 mL round bottom flask charged with a stir bar. Diethylamine (6.52 g, 89.2 mmol, 3 eq) was added via an air tight syringe directly to the reaction mixture, then heated to 90° C. and refluxed for 1.5 hours. The heat was removed and the reaction was left to stir for 24 hours at room temperature. The carboxylic acid intermediate was not isolated and was used directly in the next step. Pyridine (7.76 g, 98.1 mmol, 3.3 eq) was added directly to the solution of carboxylic acid intermediate (7.17 g, 29.7 mmol, 1 eq) and was left to stir for 10 minutes. The reaction mixture was cooled to 0° C. and then propylphosphonic anhydride (T3P) (50% by weight in THF) (37.84 g, 59.5 mmol, 2 eq) was added. The reaction was stirred under nitrogen at 0° C. for 24 hours. HCl (0.5 M, 90 mL) was added to the flask and the reaction was stirred over the weekend at room temperature. The reaction was transferred to a 500 mL separatory funnel and product was extracted with 75 mL of DCM 3 times. The organic layers were combined, dried with potassium carbonate, gravity filtered and the solvent removed under vacuum to afford 1-(diethylamino)-2-{1-[2-(diethylamino)-2-oxoethyl]cyclopentyl}-1-ethanone as a light-yellow oil (8.71 g, 29.4 mmol, 99%). The product of this first step had the expected $^1$H NMR spectra. $^1$H NMR (400 MHZ, CDCl$_3$): δ ppm: 3.32 (m, 8H), 2.63 (s, 4H), 1.7 (q, 4H), 1.6 (q, 4H), 1.13 (t, 6H), 1.07 (t, 6H).

Synthesis of 1-(diethylamino)-2-{1-[2-(diethylamino)ethyl]cyclopentyl}ethane

Lithium aluminum hydride (4.36 g, 115 mmol, 2.4 eq) was dissolved in 200 mL of anhydrous THF in a flame-dried 3-necked 1 L round bottom flask. Diamide 1-(diethylamino)-2-{1-[2-(diethylamino)-2-oxoethyl]cyclopentyl}-1-ethanone (14.2 g, 47.9 mmol, 1 eq) was dissolved in 200 mL of anhydrous THF then dripped slowly into the LiAlH$_4$/THF solution via a flame-dried dropping funnel. After all of the diamide was added, the reaction was heated to 70° C. and refluxed for 3 hours and then allowed to stir and cool to room temperature overnight. The reaction was then cooled back to 0° C. and quenched with the 1:1:3 method (1 mL of water, 1 mL of 10% aq. NaOH, 3 mL of water for each gram of LiAlH$_4$ used). The reaction was filtered through a celite pad on a medium fritted disk funnel and then the pad was rinsed with diethyl ether. The filtrate was dried with sodium sulfate and the solvent was removed under vacuum to afford 1-(diethylamino)-2-{1-[2-(diethylamino)ethyl]cyclopentyl}ethane as a clear oil. (12.10 g, 45.06 mmol, 94.5%). The product of this second step had the expected $^1$H NMR spectra. $^1$H NMR (400 MHZ, CDCl$_3$): δ ppm: 2.53 (q, 8H), 2.42 (m, 4H), 1.58 (m, 4H), 1.42 (m, 8H), 1.03 (t, 12H).

Synthesis of 2,2'-(cyclopentane-1,1-diyl)bis(N,N,N-triethylethan-1-aminium) iodide

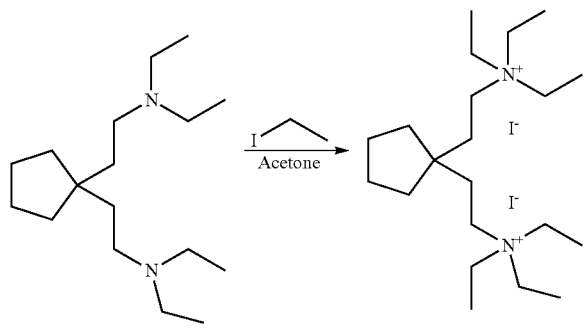

The diamine obtained from the second step of this synthesis (12.1 g, 45.1 mmol, 1 eq) was dissolved in 135 mL of acetone in a 500 mL round bottom flask. Ethyl Iodide (42.2 g, 270 mmol, 6 eq) was added to the reaction mixture via a syringe and the reaction was stirred at room temperature over the weekend. The white solid was recovered via a fritted disk funnel and washed with acetone to afford 2,2'-(cyclopentane-1,1-diyl)bis(N,N,N-triethylethan-1-aminium) iodide as a white solid (20.34 g, 35.04 mmol, 78%). The product of this third step had the expected $^1$H NMR spectra. $^1$H NMR (400 MHz, D$_2$O): δ ppm: 3.10 (q, 12H), 3.0 (m, 4H), 1.57 (m, 4H), 1.49 (m, 4H), 1.38 (m, 4H), 1.10 (t, 18H). This iodide product was converted to its hydroxide form similarly than Examples 1 and 2.

Example 6: High-Throughput Zeolite Synthesis Screening Reactions. The SDA from Examples 1-3 (C6, C5, and C6-diEt) were provided in their hydroxide forms for a series of high-throughput zeolite synthesis screening reactions with mole ratios provided in Table 4. For the high-throughput zeolite synthesis screening reactions, a 30 wt. % aqueous silica suspension (LUDOX AS-30 or AERODISP W7330) was combined with a 3.47 wt. % aqueous boric acid solution, an aqueous base solution (10 wt. % NaOH, or ~17.5 wt. % KOH), and the aqueous solution of the directing agent. The reactions were carried out in tumbling 1.5 mL stainless steel reactors tumbled at 160° C. for the reaction times indicated in Table 4. The products were isolated by centrifugation, resuspension in deionized water, and centrifugation. The process was repeated three times and the samples were collected for powder x-ray diffraction (XRD) pattern. Particular pre-synthesis ratios of the reactants and the reaction times for various samples are specified in Table 4 below.

TABLE 4

| Sample No. | DA used (Cpd) | Silica Source$^{a,b}$ | Si:B (molar) | OH:Si (molar) | SDA:Si (molar) | H$_2$O:Si (molar) | Reaction Time (days) | Result |
|---|---|---|---|---|---|---|---|---|
| 1 | I | A | 20 | K, 0.10 | 0.10 | 30 | 28 | EMM-59 |
| 2 | I | L | 10 | K, 0.10 | 0.10 | 30 | 28 | EMM-59/EUO (~70/30) |
| 3 | I | L | 10 | Na, 0.10 | 0.10 | 37 | 28 | EMM-59 |
| 4 | II | A | 20 | K, 0.10 | 0.10 | 30 | 28 | EMM-59 |
| 5 | II | L | 10 | Na, 0.10 | 0.15 | 35 | 28 | EMM-59/amorphous |
| 6 | I | A | 40 | Na, 0.10 | 0.10 | 30 | 14 | EMM-59/quartz (~50/50) |
| 7 | I | A | 20 | Na, 0.10 | 0.10 | 30 | 14 | EMM-59/minor quartz |
| 8 | I | A | 20 | K, 0.10 | 0.10 | 30 | 14 | EMM-59/EUO (~50/50) |
| 9 | I | L | 10 | K, 0.10 | 0.10 | 31 | 14 | EMM-59/EUO (~75/25) |
| 10 | I | A | 20 | Na, 0.10 | 0.10 | 30 | 7 | EMM-59 |
| 11 | I | L | 10 | Na 0.10 | 0.15 | 37 | 7 | EMM-59 |
| 12 | II | A | 20 | K, 0.10 | 0.10 | 30 | 14 | EMM-59/EUO (~50/50) |
| 13 | I | A | 20 | K, 0.15 | 0.15 | 33 | 7 | EMM-59 |
| 14 | III | A | 20 | Na, 0.10 | 0.10 | 30 | 7 | ZSM-12/EMM-59 (~60/40) |

$^a$L = LUDOX AS-30
$^b$A = AERODISP W 7330

The resulting products were found to include EMM-59, the powder XRD of which could not be matched with any known zeolite. The characterization results in Table 4 are based upon analysis of the powder XRD pattern of the product in comparison to those of EUO, quartz, and ZSM-12. Characteristic x-ray powder diffraction peaks for EUO, quartz, and ZSM-12 may be found in Collection of Simulated Powder Diffraction Patterns for Zeolites, 5$^{Th}$ revised Edition, 2007, which is incorporated herein by reference. For the screening samples, characteristic powder XRD peaks were determined using CuK-α radiation and a Bruker DaVinci D8 Discovery powder x-ray diffractometer operating in continuous mode with a Bragg-Bentano geometry and a Vantec 500 detector. Powder XRD analyses of the scaleup samples below were conducted using a Brucker D4 powder x-ray diffractometer operating in continuous mode with Cu Kα radiation and a step size of 0.01796°. The detector was a Vantec-1 gaseous detector with a 50 mm×16 mm active area.

Figure 2A:
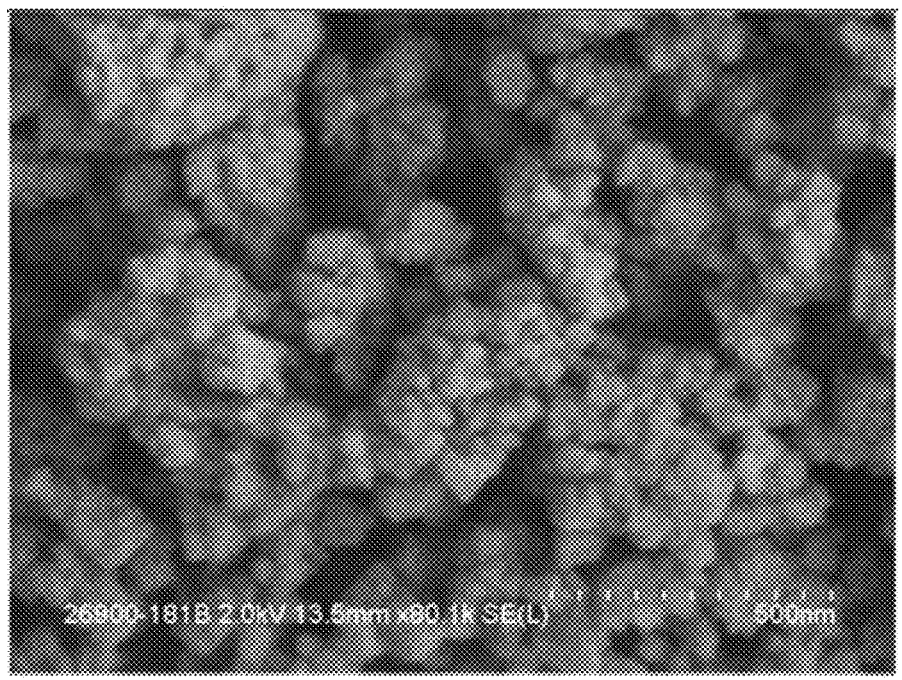
FIGS. 2A-2B show illustrative SEM images of Example 8 at various magnifications.
Figure 2B:
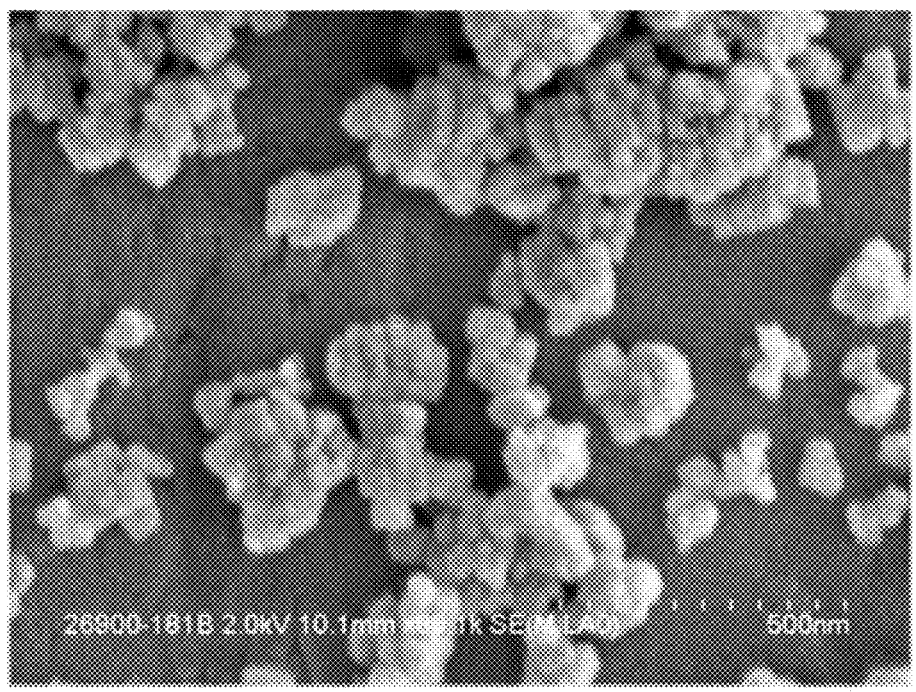

Example 7. The process of Sample 12 from Example 6 was repeated using a small amount of seeds obtained from Sample 12 of Example 6. The product was analyzed by powder XRD and was found to be pure EMM-59. FIG. 1 shows the powder XRD patterns for Example 8. FIGS. 2A-2B show illustrative SEM images of Example 8 at various magnifications.

A portion of the sample obtained in Example 7 was then calcined by first maintaining the sample at room temperature for 2 hours in nitrogen, then by ramping from room temperature to 400° C. in N2 at 4° C./min. The temperature was then held at 400° C. for 15 min before switching the environment to air. The temperature was then ramped from 400° C. to 540° C. in air at 4° C./min, and then held at 540° C. for 3 hours. Using BET analysis of nitrogen physisorption, the micopore volume, BET surface area, and external surface area of the resulting calcined product were 0.24 $cm^3/g$, 683 $m^2/g$, and 69 $m^2/g$, respectively. The material also had 0.11 mg/g uptake of n-hexane, 0.09 mg/g uptake of 2,3-dimethylbutane, 0.09 mg/g uptake of 2,2-dimethylbutane, and 0.11 mg/g uptake of mesitylene.

Figure 3:
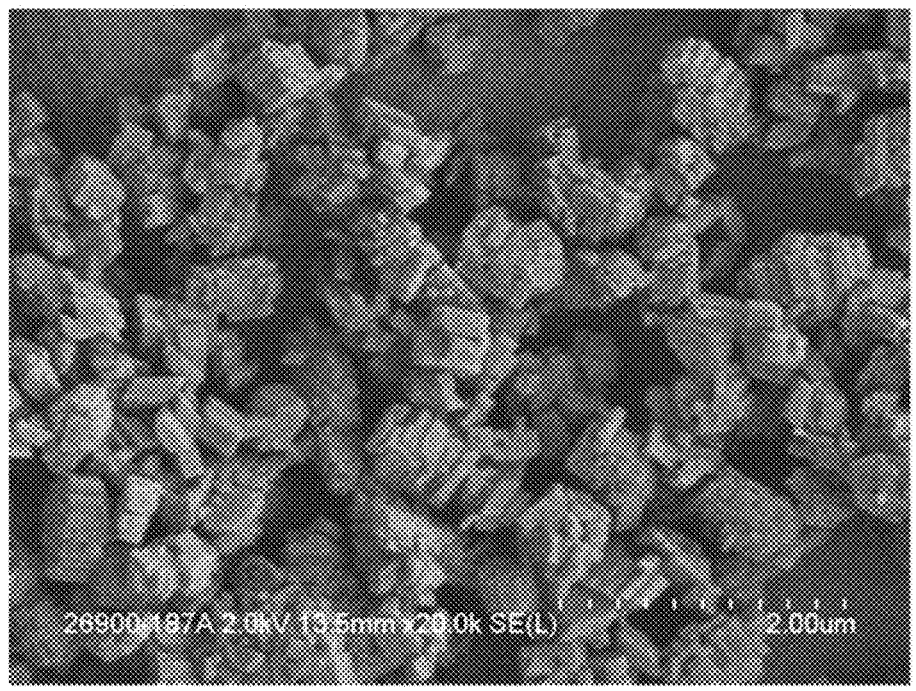
FIG. 3 shows an SEM image of the product obtained in Example 9.

Example 8. Sample 12 was synthesized at a larger scale as described below using seed crystal from Example 7. In a 60-cc overhead stirred autoclave, 11.70 g of solution containing II, 5.9 g deionized water, 1.70 g of a 17.5 wt % KOH solution, and 4.80 g of a 3.47 wt % boric solution were mixed together. 10.90 g Aerodisp W7330 colloidal silica (30 wt %) was then mixed into the solution to create a uniform suspension. Seeds of EMM-59 from Example 7 (32 mg) were added to the suspension. The mixture was then heated under overhead stirring at 180 rpm for 9 days at 150° C. Powder XRD showed the product to be pure EMM-59. FIG. 3 shows an SEM image of the product obtained in Example 8.

A portion of the sample obtained in Example 8 was then calcined using the same calcination procedure described in Example 7. Table 5 shows the characteristic powder XRD 2θ diffraction angles of Example 8 pre-calcination (as-made).

TABLE 5

| 2θ (degrees) | d-spacing (Å) | Relative Intensity |
| --- | --- | --- |
| 6.65 ± 0.1 | 13.2-13.5 | 20-35 |
| 7.35 ± 0.1 | 11.9-12.2 | 30-50 |
| 7.60 ± 0.1 | 11.5-11.8 | 35-55 |
| 8.40 ± 0.1 | 10.3-10.6 | 25-35 |
| 8.80 ± 0.1 | 9.95-10.2 | 35-45 |
| 21.0 ± 0.1 | 4.20-4.27 | 20-35 |
| 22.5 ± 0.1 | 3.92-3.96 | 25-35 |
| 22.9 ± 0.1 | 3.87-3.92 | 80-100 |
| 29.2 ± 0.1 | 3.04-3.08 | 15-25 |

Table 6 shows the characteristic powder XRD 2θ diffraction angles of Example 8 post-calcination (calcined).

TABLE 6

| 2θ (degrees) | d-spacing (Å) | Relative Intensity |
| --- | --- | --- |
| 6.55 ± 0.1 | 13.3-13.6 | 40-60 |
| 7.30 ± 0.1 | 12.0-12.2 | 85-95 |
| 7.60 ± 0.1 | 11.5-11.8 | 50-65 |
| 8.40 ± 0.1 | 10.3-10.6 | 50-65 |
| 8.85 ± 0.1 | 9.90-10.1 | 45-55 |
| 11.5 ± 0.1* | 7.60-7.65 | 15-25 |
| 14.5 ± 0.1 | 6.05-6.15 | 15-30 |
| 21.0 ± 0.1 | 4.20-4.25 | 15-30 |
| 23.0 ± 0.1 | 3.85-3.90 | 80-100 |

*This peak is a composite feature with integrated intensity greater than the absolute intensity would suggest.

Example 9. The space group and unit cell of the crystal structure of EMM-59 were determined from electron diffraction to be C2/m, a=4.0 Å, b=20.6 Å, c=16.0 Å, β=97.5°.

Example 10. Example 7 was repeated except that Compound V was used as the SDA. After 28 days, pure EMM-59 was obtained.

Example 11. Example 7 was repeated except that Compound VIII was used as the SDA. After 7 days pure EMM-59 was obtained.

Example 12. Example 7 was repeated except that Compound III was used as the SDA. After 21 days pure EMM-59 was obtained.

Example 13. Example 7 was repeated except that Compound IV was used as the SDA. After 14 days, pure EMM-59 was obtained.

Example 14. Conversion of the borosilicate EMM-59 to an aluminosilicate form. EMM-59 was ammonium and aluminum exchanged.

Ammonium exchange: 2.25 g of EMM-59 zeolite was added to 22.5 g of distilled water. To this mixture 2.25 g of ammonium nitrate was added. The mixture was stirred well, placed in a 45 mL Parr bomb, heated to 80° C. overnight, filtered, washed, and dried at 90° C. The dried material was calcined at 540° C.

Aluminum Exchange: 31.8 g of 1M aluminum nitrate solution was added to 2.12 g of EMM-59 zeolite. The mixture was well stirred and placed in a 45 mL parr bomb, heated to 80° C. overnight, filtered, washed, and dried 90° C. The final material was calcined at 540° C.

The final material had an alpha activity or 250.

All documents described herein are incorporated by reference herein for purposes of all jurisdictions where such practice is allowed, including any priority documents and/or testing procedures to the extent they are not inconsistent with this text. As is apparent from the foregoing general description and the specific embodiments, while forms of the disclosure have been illustrated and described, various modifications can be made without departing from the spirit and scope of the disclosure. Accordingly, it is not intended that the disclosure be limited thereby. For example, the compositions described herein may be free of any component, or composition not expressly recited or disclosed herein. Any method may lack any step not recited or disclosed herein. Likewise, the term "comprising" is considered synonymous with the term "including." Whenever a method, composition, element or group of elements is preceded with the transitional phrase "comprising," it is understood that we also contemplate the same composition or group of elements with transitional phrases "consisting essentially of," "consisting of," "selected from the group of consisting of," or "is" preceding the recitation of the composition, element, or elements and vice versa.

Unless otherwise indicated, all numbers expressing quantities of ingredients, properties such as molecular weight, reaction conditions, and so forth used in the present specification and associated claims are to be understood as being modified in all instances by the term "about." Accordingly, unless indicated to the contrary, the numerical parameters set forth in the following specification and attached claims are approximations that may vary depending upon the desired properties sought to be obtained by the embodiments of the present disclosure. At the very least, and not as an attempt to limit the application of the doctrine of equivalents to the scope of the claim, each numerical parameter should at least be construed in light of the number of reported significant digits and by applying ordinary rounding techniques.

Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces.

One or more illustrative embodiments are presented herein. Not all features of a physical implementation are described or shown in this application for the sake of clarity. It is understood that in the development of a physical embodiment of the present disclosure, numerous implementation-specific decisions must be made to achieve the developer's goals, such as compliance with system-related, business-related, government-related and other constraints, which vary by implementation and from time to time. While a developer's efforts might be time-consuming, such efforts would be, nevertheless, a routine undertaking for one of ordinary skill in the art and having benefit of this disclosure.

Therefore, the present disclosure is well adapted to attain the ends and advantages mentioned as well as those that are inherent therein. The particular embodiments disclosed above are illustrative only, as the present disclosure may be modified and practiced in different but equivalent manners apparent to one having ordinary skill in the art and having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present disclosure. The embodiments illustratively disclosed herein suitably may be practiced in the absence of any element that is not specifically disclosed herein and/or any optional element disclosed herein.

The invention claimed is:

1. A composition comprising:

a borosilicate zeolite, an aluminosilicate zeolite, or an aluminoborosilicate zeolite having a micropore volume of about 0.24 cm$^3$/g to about 0.28 cm$^3$/g, the borosilicate zeolite, aluminosilicate zeolite, or aluminoborosilicate zeolite being EMM-59 in calcined form, the borosilicate zeolite, aluminosilicate zeolite, or aluminoborosilicate zeolite having an X-ray diffraction pattern including d-spacings and relative intensities of:

| d-spacing (Å) | Relative Intensity |
|---|---|
| 13.3-13-6 | S |
| 12.0-12.2 | VS |
| 11.5-11.8 | S |
| 10.3-10.6 | S |
| 9.90-10.1 | S |
| 7.60-7.65 | W |
| 6.05-6.15 | W |
| 4.20-4.25 | W |
| 3.85-3.90 | VS. |

\* \* \* \* \*